(12) United States Patent
Jiang et al.

(10) Patent No.: US 8,211,704 B2
(45) Date of Patent: Jul. 3, 2012

(54) DETERMINATION METHOD OF MAGNESIUM CONTENT IN ALUMINIUM ALLOY

(75) Inventors: Ping Jiang, Chongqing (CN); Yu Chen, Chongqing (CN); Yukun Song, Chongqing (CN); Gongda Liu, Chongqing (CN); Manni Liu, Chongqing (CN); Zhihong Wei, Chongqing (CN); Jian Tang, Chongqing (CN); Hong Zhou, Chongqing (CN); Yongli Hu, Chongqing (CN)

(73) Assignee: Southwest Aluminum (Group) Co., Ltd., Chongqing (CN)

( * ) Notice: Subject to any disclaimer, the term of this patent is extended or adjusted under 35 U.S.C. 154(b) by 0 days.

(21) Appl. No.: 12/934,929

(22) PCT Filed: Jul. 15, 2008

(86) PCT No.: PCT/CN2008/071643
§ 371 (c)(1),
(2), (4) Date: Sep. 27, 2010

(87) PCT Pub. No.: WO2009/124435
PCT Pub. Date: Oct. 15, 2009

(65) Prior Publication Data
US 2011/0027895 A1     Feb. 3, 2011

(30) Foreign Application Priority Data
Apr. 8, 2008 (CN) .......................... 2008 1 0089584

(51) Int. Cl.
*G01N 33/20* (2006.01)
(52) U.S. Cl. .......................................... 436/79; 436/73
(58) Field of Classification Search .................... 436/73, 436/79
See application file for complete search history.

(56) References Cited

U.S. PATENT DOCUMENTS
4,205,953 A    6/1980  Miller
6,803,235 B1 * 10/2004 Mize et al. .................... 436/2

FOREIGN PATENT DOCUMENTS
CN    101038259 A    9/2007
WO    WO 93/08684    5/1993
WO    WO 93/08684 A  5/1993

OTHER PUBLICATIONS

Xue Fulian, "Rapid Determination of Mg in Aluminium Alloy", Shanghai Nonferrous Metals, Sep. 2002, vol. 23, No. 3, pp. 125-126 (Abstract).
Wang RuiBin, "Rapid determination of magnesium in limestone by spectrophotometry with eriochrome black", Metallurgical Analysis, Aug. 2006, vol. 25, No. 4, pp. 79-18 (Abstract).
Guo Rui, "Ammonia Water-Curron Sepowation of Variables Deter-Meination Ball Ferrum's Magnesium", Journal of Northwest Institute of Light Industry, Jun. 1996, vol. 14, No. 2, pp. 131-133.
Chen, Yong-Jao, Analytical Chemistry Series, vol. 1, Book 5, Complexometric Titration, Science Publishing Company, 1986 (Abstract).
International Search Report, PCT/CN2008/071643, Jan. 22, 2009, 2 pages.

* cited by examiner

*Primary Examiner* — Vickie Kim
*Assistant Examiner* — Dwan A Gerido
(74) *Attorney, Agent, or Firm* — Kilpatrick Townsend & Stockton LLP

(57) ABSTRACT

The present invention discloses a method for determination of magnesium content in aluminum alloy, including: dissolving an aluminum alloy sample, using one or more compounds selected from the group consisting of mercapto-containing compound, acetone cyanohydrin, β-aminoethyl mercaptan, triethanolamine, tetraethylenepentamine, ethylene diamine and oxydol as masking agent, using eriochrome black T or methyl thymol blue as indicator, and using EDTA or CDTA to titrate the sample.

7 Claims, No Drawings

DETERMINATION METHOD OF MAGNESIUM CONTENT IN ALUMINIUM ALLOY

CROSS-REFERENCES TO RELATED APPLICATIONS

The present application claims priority to PCT/CN2008/071643 filed Jul. 15, 2008 which claims priority to Chinese Patent Application No. 200810089584.9 filed Apr. 8, 2008 entitled "METHOD FOR DETERMINATION OF MAGNESIUM CONTENT IN ALUMINIUM ALLOY", incorporated by reference for all purposes.

FIELD OF THE INVENTION

The present invention relates to an analytical method, and more specifically to a method for determination of magnesium content in aluminum alloy, especially for on-the-spot rapid determination of magnesium content in aluminum alloy.

BACKGROUND ART

Determination of magnesium element content in aluminum alloy is an essential means for quality control in enterprises which produce magnesium-containing aluminum alloys. Besides instrumental analytic methods (e.g., atomic absorption spectrometry, ICP-AES method), high content of magnesium in aluminum alloy usually is determined by EDTA complexometric titration methods, currently including two major well-developed methods: copper-reagent method and potassium cyanide method. The copper-reagent method comprises two filtering separation steps resulting in complicated operation and prolonged analytical period and thus is not suitable for on-the-spot sample analysis. The potassium cyanide method is simple and rapid, conventionally used as an on-the-spot analysis method in aluminum processing factories.

Potassium cyanide is an excellent masking agent, but also a high toxic agent harmful to human beings and environment. Hence, there still is a need to find a substitute of potassium cyanide to realize a rapid cyanide-free determination of magnesium content.

SUMMARY OF THE INVENTION

The present invention provides a safe and cyanide-free method for determination of magnesium content in aluminum alloy, especially for on-the-spot rapid determination of magnesium content in aluminum alloy.

In one embodiment of the invention, it is to provide a method for determination of magnesium content in aluminum alloy, comprising the following steps: dissolving an aluminum alloy sample; and performing titration by using one or more compounds selected from the group consisting of mercapto-containing compound (such as dimercapto-succinic acid, dimercapto-propanol and mercapto-acetic acid), acetone cyanohydrin, β-aminoethyl mercaptan, triethanolamine, tetraethylenepentamine, ethylene diamine and oxydol as masking agent.

In the present invention, one or more compounds selected from the group consisting of mercapto-containing compound, acetone cyanohydrin, β-aminoethyl mercaptan, triethanolamine, tetraethylenepentamine, ethylene diamine and oxydol are used as masking agent, which can mask a large amount of aluminum and a small amount of metallic elements other than magnesium, thereby making it possible to determine magnesium content in aluminum alloy accurately and rapidly.

The inventors of the present invention found through further studies that the use of triethanolamine, tetraethylenepentamine and oxydol as a combined masking agent in particular can efficiently mask interfering elements, especially Al, Fe, Mn, Cu, Zn, Ni, Pb, Be, Ti, Cd, Co, Mn, Sb, Bi, Zr, Cr or the like present in aluminum alloy samples.

Compared with the conventional potassium cyanide method, the method of the present invention has advantages of low toxicity and low consumption thereby reducing potential hazards, management cost and environmental pollution, and thus having remarkable economic benefits and social benefits.

Moreover, preferable embodiments of the method according to the present invention further realize at least one of the following advantages: well inhibiting the hydrolysis of interfering elements in aluminum alloy, thereby eliminating the drawbacks caused by hydrolysis, such as advanced end point, easy color reversion and difficulty in accurate determination, for example, oxydol can effectively inhibit the hydrolysis of beryllium and other elements; better analytical reproducibility; reagents with low toxicity and low consumption; equivalent or even better analysis time in comparison with the potassium cyanide method; and desired comprehensive index.

The method according to the present invention can be used for on-the-spot rapid determination of magnesium content in aluminum alloy, especially suitable for on-the-spot rapid determination of large magnesium content ranging from 1.0 to 10.0% in aluminum alloys.

SPECIFIC MODES FOR CARRYING OUT THE INVENTION

In one embodiment of the present invention, it is to provide a method for determination of magnesium content in aluminum alloy, comprising the following steps: dissolving an aluminum alloy sample; and performing titration by using one or more compounds selected from the group consisting of mercapto-containing compound, acetone cyanohydrin, β-aminoethyl mercaptan, triethanolamine, tetraethylenepentamine, ethylene diamine and oxydol as masking agent.

In one preferred embodiment, it is to provide a method for determination of magnesium content in aluminum alloy, comprising the following steps: dissolving an aluminum alloy sample; and performing titration by using triethanolamine, tetraethylenepentamine and oxydol as a combined masking agent.

In the method according to the present invention, means of dissolving aluminum alloy sample is not particularly limited, and any means known in the art which can properly dissolve aluminum alloy sample can be used. For example, sodium hydroxide, hydrochloric acid, nitric acid, hydrogen peroxide, sulfuric acid, hydrofluoric acid or a mixture thereof can be used to dissolve aluminum alloy sample. However, dissolving with a mixed solution of hydrochloric acid and nitric acid is preferred. In one preferred embodiment, the mixed solution of hydrochloric acid and nitric acid contains hydrochloric acid and nitric acid mixed homogenously in a volume ratio of about 6:1, and preferably, the hydrochloric acid and the nitric acid are separately diluted with an equal volume of water. If necessary, aluminum alloy sample can be dissolved more sufficiently and rapidly by heating.

In the method according to the present invention, titrating indicator is not particularly limited, and a titrating indicator suitable for the present method can be easily chosen by one skilled in the art. For example, the titration can be performed by using an indicator selected from eriochrome black T, methyl thymol blue, K-B indicator and Calcon I, preferably eriochrome black T and K-B indicator. In one preferred embodiment of the present invention, K-B indicator is used as the titrating indicator. K-B indicator consists of acidic chrome blue K and naphthol green B. Acidic chrome blue K gives a blue color at a pH of 8-13 and becomes rose-red when chelating with a metallic ion. To make a sharp end point, an appropriate amount of naphthol green B is added as required, thus obtaining K-B indicator. In a more preferred embodiment of the method according to the invention, eriochrome black T is used as titrating indicator. Eriochrome black T gives a blue color at a pH of 8-11 and becomes red when chelating with a metallic ion, which leads to a more apparent end point.

In the method according to the present invention, the complexometric titrant used to chelate magnesium ions is not particularly limited, and can be easily chosen by one skilled in the art. For example, the titration can be performed by using CDTA (cyclohexanediaminetetraacetic acid), EDTA (ethylene diamine tetraacetic acid) or the like as complexometric titrant.

The inventors of the present invention compared EDTA with CDTA in comparative experiments and found that: CDTA was superior to EDTA in stability of the complex formed with metallic ions and had less interference factors; CDTA reacted with metallic ions at a relatively slow rate, the control of titrating speed at a changing temperature is difficult, an the analytic deviation among different analysts is relatively great. For example, when a sample contained 0.001 wt % or more of Be, the hydrolysis of Be leads to a systemic negative derivation. In addition, CDTA was more expensive than EDTA, leading to a higher analytical cost. Therefore, one skilled in the art can properly choose a titrant through a simple experiment, for example, according to the results of the above comparative experiments.

Therefore, in one particular embodiment of the invention, CDTA is used as titrant, for example, in the case where Be content is lower than 0.001 wt % or zero and/or it is required to form a more stable complex with metallic ions, In another particular embodiment of the invention, the use of EDTA as titrant can reduce cost and/or improve titrating accuracy.

In one specific embodiment of the invention, an EDTA solution is used to titrate a solution with eriochrome black T as indicator until the solution changes from red to stable bright blue, and then the magnesium content in alloy is calculated from the volume of the consumed EDTA solution.

In the method according to the present invention, the composition of buffer solution is not particularly limited, and one skilled in the art has ability to make a proper choice. For example, it is possible to use a buffer solution of ammonia nature, which preferably is an ammonia solution with dissolved ammonium chloride. The based buffer solution of ammonia nature has preferably a pH of about 9.5 to about 11, and more preferably about 10.

Taking the EDTA complexometric titration method as example, it is known that $lgK_{Mg-EDTA}=8.6>8$, and the minimal acidity for accurate titration is pH>9.5, that is to say, when pH=10, $Mg^{2+}$ can quantitatively complex with EDTA and an accuracy result can be calculated; $lgK_{mg-T}=7.0<8.6$. Eriochrome black T appears a blue colar at pH=8-11, which means that when pH=10, the complex formed with eriochrome black T and $Mg^{2+}$ can be replaced by EDTA, leading to a color change to indicate the end point. This can be expressed by the following equations:

Therefore, it is preferred to use a buffer solution with a pH ranging from about 9.5 to about 11 in the invention to perform the titrating analysis and it is relatively ideal to select a buffer solution having a pH of about 10.

In one particular embodiment of the present method, the determination of magnesium content in aluminum alloy is performed by specifically employing the following steps: dissolving an aluminum alloy with a mixed solution of hydrochloric acid and nitric acid; using triethanolamine, tetraethylenepentamine and oxydol as a combined masking agent; titrating with EDTA solution in an ammonia-based buffer solution within a pH range of about 9.5 to about 11 in the presence of eriochrome black T as indicator until the color of solution changes from red to stable bright blue; and calculating the magnesium content in the alloy through the volume of EDTA standard titrating solution consumed.

In the method according to the present invention, the amount of each reagent added can be determined by those skilled in the art through simple experiments, in which the addition amount of masking agent is determined particularly depending on the content of elements to be masked.

In one specific embodiment of the present invention, 0.5000 g of aluminum alloy sample as basis is accurately weighed, the aluminum alloy sample is dissolved with 20 mL of a mixed solution of hydrochloric acid and nitric acid, diluted to be 250 mL, 25.00 mL of testing solution is taken therefrom, 50 mL of water is added, and then 20 mL of triethanolamine solution diluted by water with a volume ratio of 1:1, 20 mL of tetraethylenepentamine solution diluted by water with a volume ratio of 1:4, 0.5-1.0 mL of oxydol and 10 mL of a buffer solution of ammonia nature having a pH value of 10 are used for titrating.

In one particular embodiment, the water used to dilute the testing solution in the summer preferably is ice water, which can increase the stability of complex.

When the titration is carried out by using two or more masking agents as a combined masking agent, their addition sequence is not particularly limited, which should be within the scope of the invention as long as the obtained effects do not depart from the spirit of the invention. Taking the combined masking agent of triethanolamine, tetraethylenepentamine and oxydol as example, the inventors of the present invention found through experiments that better effects were achieved by adding triethanolamine under acidic condition, while the influence of adding oxydol under acidic or basic condition is not significant. Therefore, it is preferred to carry out the titration by adding triethanolamine, tetraethylenepentamine, buffer solution and oxydol in sequence.

The invention will be further illustrated below in conjunction with experiments and examples to help those skilled in the art to sufficiently and comprehensively understand the present invention, but the protection scope of the present invention is limited thereby.

The sources of reagents and alloy samples used in the following experiments and examples are as follows:

Triethanolamine: Chengdu Chemical Reagent Company; Tetraethylenepentamine: Chengdu Jinshan Chemical Reagent Ltd.; Oxydol: Chongqing Chuandong Chemical Company; Eriochrome black T: Shanghai No. 3 Reagent Factory: all aluminum alloy standard samples and aluminum alloy samples: Southwest Aluminum (Group) Co., Ltd.

The percentages used here refer to weight percentages, unless otherwise definitely indicated.

1. Experiments for Effects of Different Masking Agents 1.1 Influence of triethanolamine Amount 50 mg aluminum samples were titrated by using 5 mL, 10 mL, 15 mL and 20 mL triethanolamine (triethanolamine was diluted by equal volume of water) as masking agent and EDTA as titrant, respectively. The results are summarized in Table 1.

TABLE 1

Experiments for triethanolamine amounts

| Triethanolamine level (mL) | EDTA amount (mL) | End point and conclusion |
|---|---|---|
| 5 | No end point | It was proven that 5 mL of triethanolamine was not sufficient to mask 50 mg aluminum. |
| 10 | 20.20 | Unapparent end |
| 15 | 20.00 | Better end with sudden change. |
| 20 | 20.00 | Better end with sudden change. |

The experiment results show that 15 mL of triethanolamine can completely mask 50 mg of aluminum. Since triethanolamine also has a certain ability to mask iron, manganese or the like, the amount of triethanolamine used for a sample with 50 mg of aluminum can be 20 mL.

1.2 Influence of Different Amounts of tetraethylenepentamine on the Effects of Masking Coexisting Interfering Ions The experiments were performed by constantly using 20 mL triethanolamine solution, 20 mL tetraethylenepentamine solution (tetraethylenepentamine was diluted with 4 times of water by volume), 50 mg aluminum and 3.00 mg magnesium. The results are summarized in Table 2.

TABLE 2

Masking experiments for tetraethylenepentamine

| Added interfering irons | EDTA amount (mL) | End point and conclusion |
|---|---|---|
| (1): 3 mg $Cu^{2+}$, 4 mg $Zn^{2+}$, 0.5 mg $Ni^{2+}$, 0.1 mg $Cd^{2+}$, 0.1 mg $Co^{2+}$ | 20.00 | Apparent sudden change, without color reversion |
| (2): identical to (1), further adding 0.25 mg $Pb^{2+}$ and 0.05 mg $Be^{2+}$ | 20.00 | Apparent sudden change, without color reversion |
| (3): identical to (2), further adding 0.05 mg $Ti^{3+}$ and 0.1 mg $Mn^{2+}$ | 20.00 | Apparent sudden change, without color reversion |
| (4): identical to (3), further adding 0.35 mg $Fe^{3+}$ | 20.00 | Unapparent end |
| (5): identical to (4), further adding 0.15 mg $Cr^{3+}$ | 19.70 | Advanced end, slight return, sudden change |

The experiment results indicate that tetraethylenepentamine in this medium can quantitatively mask 6% copper, 8% zinc, 1% nickel, 0.5% lead, 0.1% beryllium, 0.1% titanium, 0.2% cadmium, 0.2% cobalt and 0.2% manganese in aluminum alloy sample.

1.3 Influence of Different Amounts of Oxydol on Masking Effects

The experiments were performed by constantly using 20 mL triethanolamine solution, 20 mL tetraethylenepentamine solution, 50 mg aluminum and 3.00 mg magnesium. The results are summarized in Table 3.

TABLE 3

Masking experiments for oxydol

| Added interfering irons | Oxydol level (mL) | EDTA amount (mL) | End point and conclusion |
|---|---|---|---|
| 0.35 mg $Fe^{3+}$ | 0.5 | 20.00 | Apparent sudden change |
| 0.6 mg $Fe^{3+}$ | 0.5 | 20.20 | Unapparent sudden change, easy color reversion, indicator blocked by iron after long period of standing |
| 0.6 mg $Fe^{3+}$ | 1.0 | 20.00 | Apparent sudden change without return, blue color end point when supplementing indictor after color-fading of indictor |
| 0.15 mg $Cr^{3+}$ | 0.5 | 19.80 | Relatively apparent sudden change, slightly advanced end point |
| 0.15 mg $Cr^{3+}$ | 1.0 | 20.00 | Apparent sudden change without return, blue color end point when supplementing indictor after color-fading of indictor |
| 0.3 mg $Mn^{2+}$ 0.15 mg $Ti^{4+}$ | 1.0 | 20.00 | Apparent sudden change without return |
| 0.1 mg $Zr^{3+}$ 0.05 mg $Sb^{5+}$ 0.1 mg $Bi^{3+}$ | 1.0 | 20.00 | Apparent sudden change without return |

The results indicate that oxydol has a strong masking effect on polyvalent metallic ions, and can well inhibit their hydrolysis, thus eliminating the drawbacks caused by hydrolysis, such as advanced end point, easy color reversion and difficulty in accurate determination. 1.0 mL of oxydol can sufficiently mask such interfering ions in common aluminum alloys. Even if the content of Fe is above 1%, the content of Mn is above 0.6% and the content of Cr is above 0.3%, an accurate result is still obtained by increasing the amount of oxydol to be 2.0 mL. Excess oxydol can fade the color of indicator, which can be restored by supplementing the indictor.

1.4 Influence of Solution pH Value

A buffer solution having a pH value of 10 was used: 67.5 g of ammonium chloride was dissolved in an appropriate amount of water and 570 mL of concentrated ammonia was added. The solution was diluted to be 1 L and homogenously mixed.

The experiments were performed by adding different amounts of the buffer solution with pH=10. The results are summarized in Table 4.

TABLE 4

Experiment for the amounts of buffer solution

| Level of buffer solution with pH = 10 (mL) | EDTA amount (mL) | End point and conclusion |
|---|---|---|
| 5 | 20.00 | Apparent sudden change, accurate result |
| 10 | 20.00 | Apparent sudden change, accurate result |
| 20 | 20.20 | Apparent sudden change, slightly delayed end |
| 30 | 20.40 | Apparent sudden change, slightly delayed end |

It can be seen that under these experimental conditions, the influence of buffer solution in an amount of not greater than 20 mL is not significant. To ensure the analytical stability, the level of buffer solution in the present method is chosen to be 10 mL.

2. Method for Determination of Magnesium Content in Aluminum Alloy

The sample was dissolved with hydrochloric acid and nitric acid, and a combination of triethanolamine, tetraethylenepentamine and oxydol was used to mask interfering ions. The solution was titrated in a medium of ammonia nature having pH=10 by an EDTA standard titrating solution in the presence of eriochrome black T as indicator until the solution changed from red to stable light blue.

2.1 Reagents 2.1.1 Mixed Solution of hydrochloric acid and nitric acid:

300 mL of hydrochloric acid (diluted by equal volume of water) was homogenously mixed with 50 mL of nitric acid (diluted by equal volume of water).

2.1.2 Triethanolamine Solution:

Triethanolamine was dissolved in equal volume of water.

2.1.3 Tetraethylenepentamine Solution:

Tetraethylenepentamine was dissolved in 4 times of water by volume.

2.1.4 Oxydol: (p=1.10 g/mL)

2.1.5 Buffer Solution (pH=10):

67.5 g of ammonium chloride was dissolved in an appropriate amount of water and 570 mL of concentrated ammonia was added. The solution was diluted to be 1 L and homogenously mixed.

2.1.6 Eriochrome Black T Indicator (5 g/L): Ethanol Solution 2.1.7 EDTA Standard Titrating Solution (0.006172 mol/L):

23 g of disodium ethylene diamine tetraacetate was weighed and dissolved completely in an appropriate amount of water and then diluted to 10 L. The solution was calibrated with an alloy sample of the same brand.

2.2 Analytical Procedure 2.2.1 Sample 0.5000 g of sample was accurately weighed with a weight precision of 0.0001 g.

2.2.2 Determination

The weighed sample was placed into a 250 mL wide mouth beaker and then 20 mL of mixed solution of hydrochloric acid and nitric acid was added. The sample was heated to be completely dissolved and then was cooled to room temperature. The solution was transferred into a 250 mL volumetric flask and diluted to the scale, then homogenously mixed. 25.00 mL of testing solution was accurately measured into a 500 mL triangle beaker and 50 mL of water was added, then 20 mL of triethanolamine solution was added and mixed homogenously by shaking. Subsequently, 20 mL of tetraethylenepentamine solution, 10 mL of buffer solution, 0.5-1.0 mL of oxydol were added, and stood for 2 min. The EDTA standard titrating solution was used to titrate the solution in the presence of eriochrome black T as indicator until the color changed from red to stable light blue.

2.2.3 Calculation and Description of Analytical Results

The magnesium content is calculated as:

$$\omega(Mg) = \frac{CV \times 24.305}{m \times \frac{V_1}{V_0}} \times 100\%$$

where, C is the concentration of EDTA standard titrating solution (mol/L);

V is the volume of EDTA standard titrating solution consumed for titration (L);

m is the mass of sample weighed (g);

$V_1$ is the volume of testing solution measured, 25.00 mL;

$V_0$ is the volume of volumetric flask, 25.00 mL;

24.305 is the molar mass of magnesium (g/mol).

2.3 Experiments of Accuracy 2.3.1 Analysis of Aluminum-Magnesium Sample

The magnesium element in an aluminum-magnesium standard sample was analyzed by the potassium cyanide method and the cyanide-free method of the invention, respectively. The comparison of analytical results and end points are shown in Table 5.

TABLE 5

Comparison of analytical results and end points for analyzing the aluminum-magnesium standard sample by the potassium cyanide method and the cyanide-free method

| Sample #, alloy and standard value | Content of impurities | | | | | | | KCN method | | cyanide-free method | |
|---|---|---|---|---|---|---|---|---|---|---|---|
| | Fe | Mn | Cr | Ti | Be | Cu | Zn | Result | End point | Result | End point |
| E233(LF6) Mg6.33 | 0.44 | 0.52 | 0.14 | 0.08 | 0.005 | 0.13 | 0.16 | 6.30 | end return | 6.34 | good |
| E4113(5182) Mg4.69 | 0.27 | 0.37 | 0.05 | 0.02 | 0.001 | 0.05 | 0.14 | 4.67 | good | 4.69 | good |
| E222(LF2) Mg2.28 | 0.32 | 0.35 | 0.22 | 0.05 | | 0.10 | 0.05 | 2.29 | end return | 2.28 | good |
| E323(LC4) Mg2.14 | 0.41 | 0.32 | 0.17 | 0.05 | | 1.4 | 5.5 | 2.13 | return | 2.15 | good |
| E312(LD7) Mg1.37 | 1.2 | 0.14 | | 0.1 | Ni (1.1) | 2.5 | 0.24 | 1.39 | blue-green end | 1.36 | apparent sudden change, indicator with fading-color |
| LF11 Mg5.32 | 0.36 | 0.48 | | | | | | 5.33 | end return | 5.32 | apparent |
| E232(LF5) Mg5.44 | 0.351 | 0.365 | | 0.044 | 0.0028 | 0.092 | 0.15 | 5.40 | end return | 5.41 | apparent |
| E221b(LF3) Mg3.95 | 0.20 | 0.17 | 0.25 | 0.30 | | 0.045 | 0.10 | 3.92 | apparent | 3.96 | apparent |
| E123a(LY12) Mg1.51 | 0.35 | 0.53 | | 0.04 | | 4.11 | 0.15 | 1.53 | apparent | 1.51 | apparent |
| E4111(5052) Mg2.58 | 0.29 | 0.04 | 0.23 | 0.02 | | 0.03 | 0.03 | 2.60 | apparent | 2.58 | apparent |
| E4112(5083) Mg4.63 | 0.29 | 0.55 | 0.09 | 0.07 | 0.0012 | 0.03 | 0.09 | 4.61 | end return | 4.60 | apparent |
| E935(2A12) Mg1.78 | 0.42 | 0.70 | | 0.08 | | 3.90 | 0.28 | 1.79 | apparent | 1.78 | apparent |

From the comparative results in the table, it can be seen that the analytical results for the cyanide-free method of the present invention are in agreement with the standard values with deviations far lower than the chemical admissible error. Moreover, the end points for the cyanide-free method are more apparent and easier to be determined.

2.3.2 Analysis of aluminum-magnesium Alloy Sample

The standard copper-reagent method and potassium cyanide method and the cyanide-free method of this invention were respectively used to analyze different alloy samples. The comparison of analytical results thereof and the deviations of average values for the results of the cyanide-free method and the former two methods are shown in Table 6.

TABLE 6

Comparison of results of the magnesium content in sample analyzed by three analytical methods

| Sample No. | Alloy | Copper-reagent method | KCN method | Cyanide-free method | Deviation |
|---|---|---|---|---|---|
| 7041058 | 5154 | 3.60 | 3.62 | 3.58 | −0.03 |
| 7012804 | 5083 | 4.38 | 4.35 | 4.38 | +0.02 |
| 7012802 | 5A06 | 6.20 | 6.22 | 6.21 | 0 |
| 6040912 | 5A05 | 5.01 | 5.11 | 5.07 | +0.01 |
| 7012781 | 5A05 | 5.15 | 5.13 | 5.19 | +0.05 |
| 7221987 | 5182 | 4.51 | 4.53 | 4.50 | −0.02 |
| 6021572 | 5A03 | 3.84 | 3.78 | 3.84 | −0.03 |
| 6021572 | 5A03 | 3.47 | 3.39 | 3.48 | +0.05 |
| 6040834 | 7050 | 2.27 | 2.25 | 2.23 | −0.03 |
| 7041624 | 2124 | 1.58 | 1.56 | 1.57 | 0 |
| 7030894 | LF2 | 2.26 | 2.28 | 2.28 | +0.01 |
| 7054146 | 7B04 | 1.98 | 2.00 | 1.97 | −0.02 |
| 7041631 | 7050 | 2.58 | 2.54 | 2.55 | −0.01 |

TABLE 6-continued

Comparison of results of the magnesium content in sample analyzed by three analytical methods

| Sample No. | Alloy | Copper-reagent method | KCN method | Cyanide-free method | Deviation |
|---|---|---|---|---|---|
| 7231456 | 5754 | 2.90 | 2.96 | 2.97 | +0.03 |
| 7041722 | 2D70 | 1.73 | 1.71 | 1.74 | +0.02 |
| 7022620 | PX99 | 2.25 | 2.21 | 2.20 | −0.03 |
| 6040855 | 919 | 1.67 | 1.65 | 1.68 | +0.02 |
| 6021612 | 7075 | 2.38 | 2.42 | 2.38 | −0.02 |
| 6040854 | LC9 | 2.60 | 2.60 | 2.58 | −0.02 |
| 7310524 | 5052 | 2.48 | 2.44 | 2.45 | −0.01 |
| 7022540 | 7021 | 1.35 | 1.33 | 1.35 | +0.01 |
| 7013648 | 2A12-6 | 1.73 | 1.73 | 1.72 | −0.01 |
| 6053363 | 5A06 | 6.24 | 6.28 | 6.28 | +0.02 |
| 6053417 | LF6 | 6.79 | 6.87 | 6.76 | −0.07 |
| 6053369 | 5083 | 4.09 | 4.05 | 4.09 | +0.02 |
| 6021569 | 5A06 | 6.54 | 6.60 | 6.54 | −0.02 |
| 7030043 | LF5 | 5.35 | 5.31 | 5.34 | +0.01 |
| 7030042 | LF5 | 4.92 | 4.98 | 4.92 | −0.03 |

It can be seen from the above comparison results that there is no system deviation among these three analytical methods (due to the exist of both positive and negative deviations) and the deviations are also far lower than that allowed by the national standard.

2.4 Experiments for Analytical Precision

The precisions of analyzing various aluminum-magnesium alloy samples by the cyanide-free method of the invention are shown in Table 7.

TABLE 7

Experiments for analytical precision of aluminum-magnesium alloy samples

| Sample No. | Alloy | 1 | 2 | 3 | 4 | 5 | 6 | Average | Standard deviation | Fluctuation coefficient |
|---|---|---|---|---|---|---|---|---|---|---|
| 11 | LF5 | 5.31 | 5.28 | 5.31 | 5.32 | 5.34 | 5.28 | 5.32 | 0.028 | 0.53 |
| E4113 | 5182 | 4.68 | 4.69 | 4.65 | 4.66 | 4.69 | 4.65 | 4.67 | 0.019 | 0.41 |
| E233 | LF6 | 6.31 | 6.33 | 6.33 | 6.35 | 6.32 | 6.33 | 6.33 | 0.013 | 0.21 |
| E4116 | 7050 | 2.28 | 2.26 | 2.28 | 2.28 | 2.29 | 2.27 | 2.28 | 0.011 | 0.48 |
| E4111 | 5052 | 2.55 | 2.58 | 2.58 | 2.56 | 2.60 | 2.57 | 2.57 | 0.018 | 0.70 |
| E935 | LY12 | 1.78 | 1.75 | 1.77 | 1.78 | 1.76 | 1.77 | 1.77 | 0.012 | 0.68 |
| E236 | LF3 | 3.76 | 3.74 | 3.79 | 3.76 | 3.75 | 3.78 | 3.76 | 0.019 | 0.51 |
| E312 | LD7 | 1.36 | 1.37 | 1.37 | 1.36 | 1.38 | 1.37 | 1.37 | 0.011 | 0.80 |
| E323a | LC4 | 2.10 | 2.08 | 2.10 | 2.12 | 2.09 | 2.13 | 2.10 | 0.019 | 0.90 |

It can be seen from the above table that the present method has good reproducibility, high analytical precision and is suitable for on-the-spot composition control.

Although the methods of the present invention have been specifically described in detail above, it should not be understood that the method of the present invention comprises only the steps and/or materials described above. One skilled in the art can determine to add, change or delete a certain step and/or add, change or delete materials used in specific steps according to specific circumstances in order to achieve better effects, which can be achieved by those skilled in the art through a limited number of simple experiments and will not depart from the spirit and scope of the present invention. For example, NaOH solution can be used to dissolve and remove aluminum, zinc or the like in an aluminum-magnesium alloy sample, and then the resultant hydroxide precipitate containing magnesium and other ingredients is dissolved in a mixed solution of hydrochloric acid and nitric acid for further titration. The amounts of various reagents required for titration can also be adjusted depending on possible amounts of interfering ions in testing solution.

What is claimed is:

1. A method for determination of magnesium content in aluminum alloy, comprising the following steps:
    dissolving an aluminum alloy sample;
    performing titration by using triethanolamine, tetraethylenepentamine, and oxydol as a combined masking agent; and
    determining the magnesium content in the aluminum alloy.

2. The method according to claim 1, wherein the step of dissolving comprises dissolving the aluminum alloy sample with a mixed solution of hydrochloric acid and nitric acid, the mixed solution of hydrochloric acid and nitric acid contains hydrochloric acid and nitric acid mixed homogenously with a volume ratio of about 6:1, and the hydrochloric acid and the nitric acid are separately diluted with an equal volume of water.

3. The method according to claim 1, wherein the titration is performed by using methyl thymol blue as indicator.

4. The method according to claim 1, wherein EDTA or CDTA is used for titrating the magnesium content.

5. The method according to claim 1, wherein the titration is performed in a buffer solution of ammonia nature within a pH ranging from about 9.5 to about 11, and the buffer solution of ammonia nature is an ammonia solution with dissolved ammonium chloride.

6. The process according to claim 5, wherein the titration is performed by adding triethanolamine, tetraethylenepentamine, buffer solution and oxydol in sequence.

7. The process according to claim 6, wherein 0.5000 g of aluminum alloy sample as basis is accurately weighed, the aluminum alloy sample is dissolved with 20 mL of a mixed solution of hydrochloric acid and nitric acid and then diluted to be 250 mL; 25.00 mL of testing solution is taken therefrom and 50 mL of water is added; and then 20 mL of triethanolamine solution diluted by water with a volume ratio of 1:1, 20 mL of tetraethylenepentamine solution diluted by water with a volume ratio of 1:4, 0.5-1.0 mL of oxydol and 10 mL of buffer solution of ammonia nature having a pH value of 10 are used to perform the titration.

\* \* \* \* \*